United States Patent [19]
Barbee

[11] Patent Number: 5,122,056
[45] Date of Patent: Jun. 16, 1992

[54] LOCAL ANESTHETIC APPLICATOR

[76] Inventor: Carl A. Barbee, P.O. Box 509, Hailey, Id. 83333

[21] Appl. No.: 678,716

[22] Filed: Apr. 1, 1991

[51] Int. Cl.⁵ ............................................. A61G 17/02
[52] U.S. Cl. ..................................... 433/80; 433/90; 128/62 A; 604/310
[58] Field of Search ............................ 433/80, 89, 90; 128/62 A; 604/310, 311

[56] References Cited

U.S. PATENT DOCUMENTS

| | | | |
|---|---|---|---|
| 683,075 | 9/1901 | Schneider | 433/90 |
| 1,500,107 | 7/1924 | Chandler | 433/80 |
| 1,660,096 | 2/1928 | Schiele | 128/62 A |
| 2,187,560 | 1/1940 | Reilly | 128/62 A |
| 2,349,607 | 5/1944 | Berger | 433/80 |
| 2,452,903 | 11/1948 | Coffey | 433/80 |
| 2,754,590 | 7/1956 | Cohen | 433/90 |
| 3,029,809 | 4/1962 | Madlung | 128/62 A |
| 3,109,192 | 11/1963 | Levenson | 128/62 A |
| 3,242,519 | 3/1966 | Murray | 128/62 A |
| 3,267,512 | 8/1966 | Wiley | 15/561 |
| 3,401,690 | 9/1968 | Martin | 128/62 A |
| 4,194,290 | 3/1980 | Vallhonrat | 433/141 |
| 4,472,141 | 9/1984 | Dragan | 433/90 |
| 4,620,528 | 11/1986 | Arraval | 128/62 A |
| 4,628,564 | 12/1986 | Youssef | 15/167 R |

Primary Examiner—John J. Wilson
Attorney, Agent, or Firm—Frank J. Dykas; Craig M. Korfanta; Ken J. Pedersen

[57] ABSTRACT

An applicator to deliver and hold anesthetic to the gums of a teething infant. In a first embodiment, an open ended trough having a sponge lining has a handle, so that medicament may be applied to the sponge lining and then held against the gum. In a second embodiment, a tube and syringe are provided in place of the handle, and the trough has a passage where the tube attaches, so that medicament within the syringe may be measurably delivered and held to the gum. Handle and tube may be flexible, or if not flexible, attached to the trough by a joint. Orientation of the handle is preferably within 44 and 96 degrees from a normal to the trough.

9 Claims, 2 Drawing Sheets

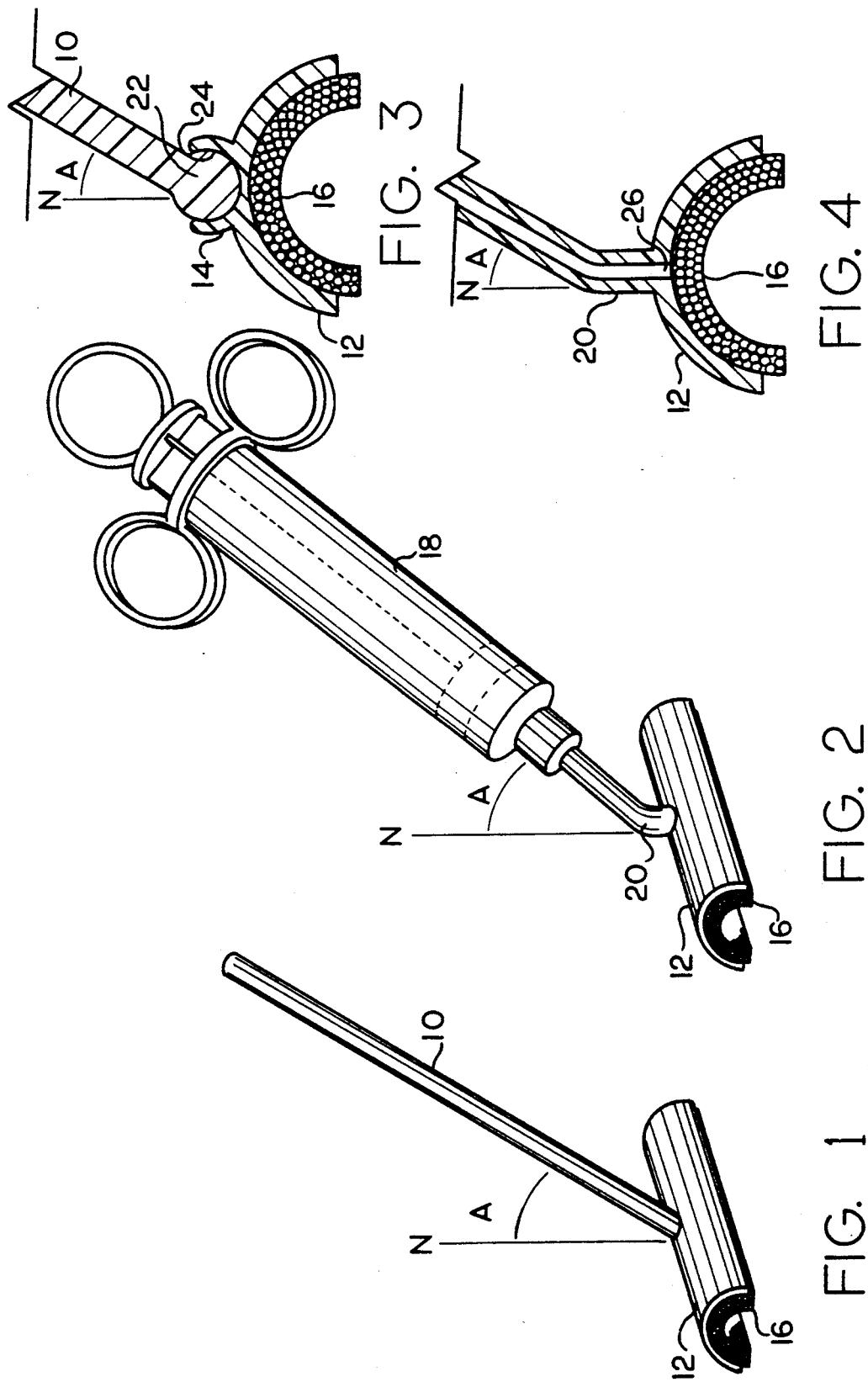

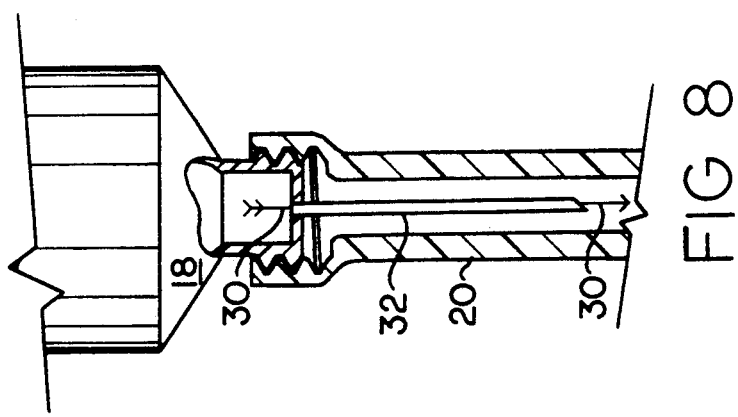
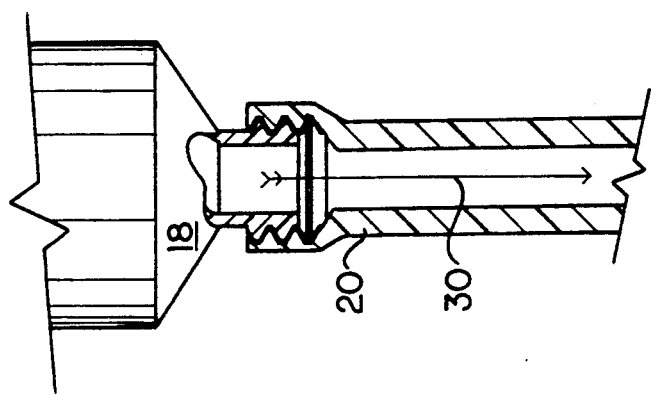
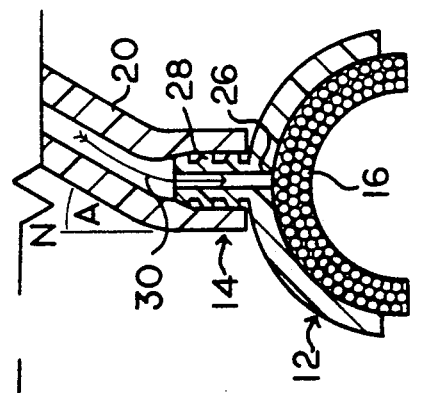
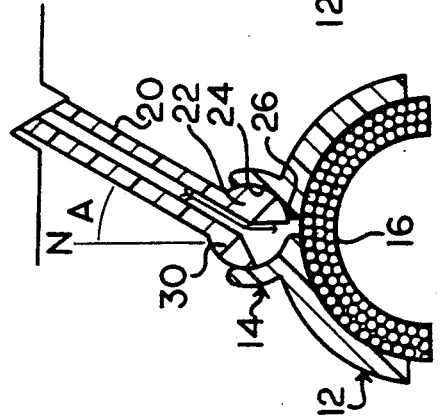

LOCAL ANESTHETIC APPLICATOR

BACKGROUND OF THE INVENTION

1. Technical Field

This invention relates generally to applicators of oral anesthetic and specifically to the local application and holding of anesthetic to the gums of a teething infant.

2. Background Art

The miseries of a teething infant and those in its vicinity are universally known.

The effectiveness of simply rubbing or otherwise distributing anesthetic on the gums is offset by the fact that it quickly dissipates into the rest of the mouth. It is also possible to deliver too much anesthetic. For example, too much 2% xylocaine gel (a common prescription anesthetic) will cause seizures.

It is desirable to have a device locally deliver anesthetic to an infant's gums, and to hold it there, preventing dissipation into the rest of the mouth. It is also desirable in the same device to be able to accurately deliver a specific amount of said anesthetic.

Dentifrice and medicament applicators are known, but an applicator which satisfies these desires is not found.

U.S. Pat. No. 4,628,564, issued Dec. 16, 1986 to Youssef, herein incorporated by reference, shows a toothbrush with a liquid-storing sponge for improved tooth cleaning.

U.S. Pat. No. 4,620,528, issued Nov. 4, 1986 to Arraval, herein incorporated by reference, teaches a toothbrush which fits on a fingertip and has a bulb reservoir so that fluid can be squeezed into the toothbrush as it is being used.

U.S. Pat. No 4,472,141, issued Sep. 18, 1984 to Dragan, herein incorporated by reference, shows an all purpose gun-like dental syringe which can be used to administer anesthesia.

U.S. Pat. No. 4,194,290, issued Mar. 25, 1980 to Vallhourst, herein incorporated by reference, teaches a disposable tooth cleaning implement for flossing, picking, and cleaning with a foam pad or brush.

U.S. Pat. No. 3,267,512, issued Aug. 23, 1966 to Wiley, herein incorporated by reference, teaches an improved disposable folded sponge type toothbrush having recesses in the inside faces of the folded sponge to carry dentifrice or mouth medicaments.

U.S. Pat. No. 2,754,590, issued Jul. 17, 1956 to Cohen, herein incorporated by reference, teaches a piston and cylinder to apply a preservative pain-inhibiting composition to the teeth until the services of a dentist can be had.

U.S. Pat. No. 683,075, issued Sep. 24, 1901 to Schneider, herein incorporated by reference, shows a syringe which is attached to a curved tube shaped to correspond with the rows of teeth, for distribution of mouthwash, disinfecting liquid, or the like, to the teeth.

DISCLOSURE OF INVENTION

In a first embodiment, an open ended trough having a sponge lining has a handle, so that medicament may be applied to the sponge lining and then held against the gum of the teething infant.

In a second embodiment, a tube and syringe are provided in place of the handle, and the trough has a passage where the tube attaches, so that medicament within the syringe may be measurably delivered and held to the gum. Handle and tube may be flexible, or if not flexible, attached to the trough by a joint.

BRIEF DESCRIPTION OF THE DRAWINGS

FIG. 1 shows a first embodiment.
FIG. 2 shows a second embodiment.
FIGS. 3-6 detail acceptable variations in the joint.
FIGS. 7-8 detail how the syringe may be attached.

BEST MODE FOR CARRYING OUT INVENTION

As shown in FIG. 1, a first embodiment of the inventive applicator includes handle 10, attached to delivery portion 12. Delivery portion 12 is in the form of a trough with open ends, able to accommodate an infant's gum within it, and has a sponge lining 16. Handle 10 is situated at an angle A from reference N normal to delivery portion 12. Handle 10 is flexible enough to allow positioning of trough 12 to any portion of the baby's gums.

In use, a measured amount of anesthetic, such as 2% xylocaine gel, is dispensed onto sponge lining 16, and is applied to the ailing gum by holding handle 10 and mating trough 12 to the gum.

FIG. 2 shows a second embodiment, where handle 10 is replaced by syringe 18 and tube 20. In this embodiment, an accurate measurable amount of anesthetic is dispensed directly from within syringe 18 through tube 20, and into and through sponge lining 16 while trough 12 is held in mating relationship with the ailing gum.

FIG. 3 illustrates how a joint 14 may be incorporated, socket 22 engaging ball 24. This makes possible higher rigidity in handle 10 while preserving maneuverability within the mouth.

As shown in FIG. 4, flexible tube 20 may be integrally formed with trough 12.

FIG. 5 shows how ball 22 and socket 24 may accommodate tube 20. Trough 12 has passage 26 to accept delivery into sponge lining 16. The delivery path is illustrated by arrow 30.

FIG. 6 shows tube 20 installed around nipple 28. Trough 12 has passage 26 to accept delivery into sponge lining 16.

Tube 20 attaches to syringe 18 by slipping around it, for example, as detailed in FIGS. 7-8. Syringe 18 of FIG. 7 has no needle. FIG. 8 shows how syringe 18 with needle 32 may be used. This embodiment is handy as a conventional hypodermic syringe may be used to withdraw a measured amount of anesthetic from a conventional medical bottle having a sealed rubber stopper, and then fitted into tube 20 for delivery to the gum. Alternatively, tube 20 may have a sealed end, requiring needle 32 to pierce it for delivery.

We wish it to be understood that handle 10 and joint 14 must be rigid enough to hold trough 12 against the gum. Tube 20 may be flexible or rigid, so long as enough rigidity is preserved for holding trough 12 against the gum. Angle A may be fixed or variable, but is preferably within 44 to 96 degrees. The inventive applicator is preferably made out of plastic by well known methods and machinery, but other constructions are possible. Trough 12 is preferably around 1.0 cm long and 8 mm wide and is substantially semi-circular in cross section, as shown in the drawings. Handle 10 is preferably about 4 cm long.

We also wish it to be understood that this invention may also be used to deliver medicament other than an anesthetic to the gums of adults as well as children.

While there is shown and described the present preferred embodiment of the invention, it is to be distinctly understood that this invention is not limited thereto but may be variously embodied to practice within the scope of the following claims.

I claim:

1. A device to apply medicament to a gum, comprising:
   an open ended trough, about 8 millimeters wide and about 1.0 centimeters long, having a sponge lining;
   a handle, about 4 centimeters long, integrally formed with said trough, and oriented within 44 and 96 degrees from a normal to said trough; and
   so that medicament may be applied to said sponge lining and then held to the gum.

2. A device to apply medicament to a gum, comprising:
   an open ended trough, having a sponge lining, sized to mate with the gum; and
   a handle attached to said trough, wherein said handle is flexibly oriented within 44 and 96 degrees from a normal to said trough so that medicament may be applied to said sponge lining and then held to the gum.

3. A device to apply medicament to a gum, comprising:
   an open ended trough, having a sponge lining, sized to mate with the gum; and
   a handle attached to said trough, wherein said handle is attached to said trough by a joint, and able by said joint to be oriented within 44 and 96 degrees from a normal to said trough so that medicament may be applied to said sponge lining and then held to the gum.

4. A device to apply medicament to a gum, comprising:
   an open ended trough, having a sponge lining, sized to mate with the gum; and
   a handle attached to said trough, wherein said handle is about 4 centimeters long, and said trough is about 8 millimeters wide and about 1.0 centimeters long so that medicament may be applied to said sponge lining and then held to the gum.

5. A device to apply medicament to a gum, comprising:
   an open ended trough, having a sponge lining, sized to mate with the gum;
   a tube, having a first end attached to said trough; a syringe attached to a second end of said tube, so that any medicament contained in said syringe may be measurably delivered and held to the gum;
   a passage in said trough where said tube attaches; and
   so that medicament may be delivered through said tube, said passage, and said sponge lining to the gum, and so that the medicament may be delivered and held to the gum.

6. A device to apply medicament to a gum, comprising:
   an open ended trough, having a sponge lining, sized to mate with the gum;
   a tube, having a first end attached to said trough;
   a passage in said trough where said tube attaches;
   a syringe attached to a second end of said tube; and
   so that medicament may be delivered from within said syringe through said tube, said passage, and said sponge lining to the gum, and so that the medicament may be delivered and held to the gum.

7. A device to apply medicament to a gum, comprising:
   an open ended trough, about 8 millimeters wide and about 1.0 centimeters long, having a sponge lining which contains a medicament;
   a handle, about 4 centimeters long, integrally formed with said trough, and oriented within 44 and 96 degrees from a normal to said trough; and
   so that said medicament may be held to the gum.

8. The device of claim 7, wherein said medicament is selected from the group consisting of 2% xylocaine or Benzocaine.

9. A device to apply medicament to a gum, comprising:
   an open ended trough, having a sponge lining, sized to mate with the gum;
   a rigid tube, having a first end for attachment to a ball and socket joint;
   a ball and socket joint attaching said first end of the rigid tube to said trough, said ball and socket joint having a passage therethrough in alignment with where the tube attaches;
   a trough passage in said trough where said ball and socket joint attaches; and
   so that medicament may be delivered through said tube, said passage in the ball and socket joint, said trough passage, and said sponge lining to the gum, and so that the medicament may be delivered and held to the gum.

* * * * *